United States Patent [19]

Seiler et al.

[11] 4,173,576

[45] Nov. 6, 1979

[54] PROCESS FOR THE ESTERIFICATION OF CHLOROSILANES

[75] Inventors: Claus-Dieter Seiler, Rheinfelden; Hans-Joachim Vahlensieck, Wehr; Hans-Joachim Kötzsch, Rheinfelden, all of Fed. Rep. of Germany

[73] Assignee: Dynamit Nobel Aktiengesellschaft, Troisdorf, Fed. Rep. of Germany

[21] Appl. No.: 882,000

[22] Filed: Feb. 28, 1978

Related U.S. Application Data

[63] Continuation of Ser. No. 707,454, Jul. 21, 1976, abandoned.

[30] Foreign Application Priority Data

Jul. 23, 1975 [DE] Fed. Rep. of Germany ....... 2532887

[51] Int. Cl.$^2$ .......................... C07F 7/18; C07F 7/04; C07F 7/06
[52] U.S. Cl. ...................... 260/448.8 R; 260/448.8 A
[58] Field of Search ................ 260/448.8 R, 448.8 A

[56] References Cited

U.S. PATENT DOCUMENTS

| 3,008,975 | 11/1961 | Shubert | 260/448.8 R |
|---|---|---|---|
| 3,985,781 | 10/1976 | Kotzsch et al. | 260/448.8 R |

*Primary Examiner*—Paul F. Shaver
*Attorney, Agent, or Firm*—Sprung, Felfe, Horn, Lynch & Kramer

[57] ABSTRACT

An improvement in the process for the esterification of chlorosilanes with alcohols wherein the esterification is carried out in the presence of a chlorohydrocarbon and in the absence of an acid binding agent.

12 Claims, No Drawings

PROCESS FOR THE ESTERIFICATION OF CHLOROSILANES

This is a continuation filed 707,454 filed July 21, 1976, now abandoned.

BACKGROUND OF THE INVENTION

1. Field of the Invention

This invention relates to an improvement in the process for preparation of alkoxysilanes by the esterification of chlorosilanes with alcohols. More especially, this invention relates to the preparation of higher yields of alkoxysilane by the esterification of chlorosilanes with alcohols wherein the process is carried out in the presence of a chlorohydrocarbon and in the absence of an acid binding agent.

2. Discussion of the Prior Art

Esterification of chlorosilanes with alcohols en route to the preparation of alkoxysilanes is known and takes place in accordance with the following equation:

$$R_mSiCl_{4-m} + nR'OH \rightarrow R_mSi(OR')_nCl_{4-m-n} + nHCl.$$

In this equation, R' represents an alkyl radical of 1 to 11 carbon atoms, m is a value of between 0 and 3, n is a value of between 1 and 4 and R represents hydrogen or a $C_1$-$C_{11}$ alkyl radical.

Difficulties have been encountered in the practical performance in that the hydrogen chloride that is formed in large amounts due to the process, not only cleaves the alkoxy group to alcohol and chlorosilanes but also, especially in the presence of alkanol, cleaves the hydrogen silane bond to yield hydrogen and form an alkoxysilane chlorosilane bond. Furthermore, the hydrogen chloride forms chloroalkanes with the alkanols employed, and intermediately forms water. This water, in turn, tends to hydrolyze the chlorosilanes and alkoxysilanes into hydrolyzates. Unless certain process conditions are formed, the desired ester is usually entirely lost.

As a consequence thereof, a number of attempts have been made to prepare such compounds in a more economical manner. The weakness of the formation of condensate, which originally encumbered the batch processes, due to the aforementioned secondary reactions of HCl with alcohols in the esterification can be largely avoided by the use of modern batch methods. However, these modern methods are limited to the application of those methods which can be performed on a large, commercial scale, inasmuch as systems must be provided to control the large amounts of HCl realized, especially in conjunction with the low boiling temperatures of the starting substances employed and the rapid and severe temperature gradients which are required, both in the reaction chamber and in the exhaust gas, if the reaction is to be conducted safely.

Continuous processes have also been proposed wherein chlorosilanes are esterified in the liquid phase in a reactor equipped with an overflow borrowed from the simple batch technology art. Continuous processes have also been proposed employing a plurality of reactors connected in series in a somewhat countercurrent principle. This type of process, however, has the disadvantage that the hydrogen chloride is removed too slowly and incompletely. This results in the re-cleavage of already formed ester groups and in the commencement of secondary reactions between the alcohols and the hydrogen chloride, with the undesired formation of hydrolyzates.

Another proposed esterification procedure of the chlorosilanes with alcohols has involved the use of a gas phase and temperatures which are above the boiling points of all substances involved, i.e., above the boiling points of both the starting products and the desired end products. This process has, however, the decided disadvantage in that elevated temperatures are required which cause the hydrogen chloride present in the system to produce a particularly rapid promotion of the known secondary reactions. This catalytic effect upon the secondary reactions effects a re-cleavage, alcohol dehydration and the formation of the hydrolyzate.

The particular weaknesses of all of the continuous esterification processes described above lies in the fact that excessively low and incomplete separation of the hydrogen chloride from the reaction mixture is involved. It has already been proposed, therefore, to purge out the HCl forming as a result of the process by passing inert gases, such as nitrogen, over the surface of or through the reaction mixture with the aid, in some cases, of a falling film evaporator. Where such evaporator is employed, an upper temperature limit must not be exceeded. This general procedure, however, has the considerable disadvantage in that the exhaust gas volume, which contains HCl, is enormously increased and vaporization losses ensue. The loss of the material through vaporization losses is determined by the partial pressure of the products. These losses become unreasonably high and virtually preclude the reuse of hydrogen chloride given off as a result of the process.

Furthermore, in the foregoing procedure, powerful cooling apparatus are necessary to reduce the product loss in the inert gas stream. Additionally, extremely dry gases are essential to such a procedure, unless otherwise the formation of siloxanes is intensified.

It is further known to increase the rate of withdrawal of HCl and other hydrogen halides from the reaction mixture during the esterification process by the addition of benzolic or benzinic solvents to the halogen silane, in order thereby to diminish the above-described formation of siloxanes. In spite of these measures, appreciable residual acidites remain in the reaction product in these procedures and they must be counteracted by the addition of acid binding substances such as salts. This addition entails the disadvantage of the need for additional procedures and materials, as well as the filtration of the raw ester and the elution of the salts to reduce the yield losses.

The esterification of chlorosilanes with alcohols is known to proceed in the presence of chlorinated hydrocarbon, wherein the introduction of tertiary alcoholic components in the presence of amines is performed. In this procedure, however, large amounts of salts are also produced which must be removed by additional processing steps.

It therefore has become desirable to provide a simple and effective means for realizing high yields of desired esterification product of chlorosilanes with alkanols. More especially, it has become desirable to provide a process in which efficient removal of HCl formed during the process is ensured thereby precluding the HCl from entering into secondary reactions. More especially, it has become desirable to provide a process for preparing higher yields of desired alkoxysilane by the reduction of secondary reactions.

SUMMARY OF THE INVENTION

The foregoing long-felt desideratum are provided, in accordance with the invention, by an improved process for the esterification of chlorosilanes wherein a chlorosilane is reacted with an alcohol. The improvement lies in the fact that the process is carried out in the presence of a chlorinated hydrocarbon and in the absence of an acid binding agent. It has been discovered, quite surprisingly, that by simply carrying out the alkoxysilane preparation in the presence of a halogenated hydrocarbon and in the absence of an acid binding agent that exceptionally high yields of alkoxysilane can be provided in a greatly simplified process. The increase in yield is startingly surprising especially considering the simple manipulative procedures which characterize the improved process. The unexpected increase in yield applies to chlorosilane esterifications employing both primary and secondary alcohols as well as phenols.

The reaction takes place in accordance with the above equation. Suitable starting substances of the general formula $R_m SiCl_{4-m}$ are, for example, trichlorosilane, tetrachlorosilane, methyldichlorosilane, trimethylchlorosilane, methyltrichlorosilane, ethyltrichlorosilane, ethyldichlorosilane, n-propyldichlorosilane, propyltrichlorosilane, isobutyldichlorosilane, vinyldichlorosilane, vinyltrichlorosilane, vinylmethyldichlorosilane, dimethyldichlorosilane, propenyltrichlorosilane, allyltrichlorosilane, 3-chloropropyltrichlorosilane, etc. From this it appears that R can represent both saturated and unsaturated alkyl radicals of up to eleven, and preferably up to 6 carbon atoms, and also hydrogen. The alkyl radicals can also be different, as in the case for example of methylethyldichlorosilane or methylphenyldichlorosilane. Phenyltrichlorosilane can also be used. The radical R can also be substituted by halogen, as in the case, for example, of chloropropyltrichlorosilane, chloroethyltrichlorosilane, methylchloroethyltrichlorisilane, or $CF_3$—$CH_2$—$SiCl_3$ or even $CF_3$—$CH_2$—$O$—$(CH_2)_3$—$SiCl_3$.

The alcohols of the general formula R'OH for the preparation of the silane esters can be simple aliphatic alcohols, examples of which are methanol, ethanol, n-propanol, n-butanol, or octanol, but also, for example, 2-methoxyethanol, 2-ethoxyethanol, tetrahydrofurfuryl alcohol, 2-methoxyethyldiethyleneglycol ether or polyethyleneglycol monoether.

The radical R' can accordingly be a straight-chain or cyclic alkyl radical interrupted by hetero atoms such as —O— or —N—. The corresponding secondary alcohols or phenols, or even mixed aromatic-aliphatic alcohols such as benzyl alcohol, can also be used.

Usable chlorinated hydrocarbons are compounds such as carbon tetrachloride, chloroform, methylene chloride, dichloroethane, dichloroethylene, 1,1,1-trichloroethane, trichloroethylene, perchloroethylene and tetrachloroethane.

Generally, chlorinated hydrocarbons useful in accordance with the present process are those which are fluid under normal conditions and have a boiling point below 150° C. The number of hydrocarbons in the chlorinated hydrocarbon is preferably in the range of from 1 to 5. The hydrocarbon radical itself can either be saturated or unsaturated. In addition to those chlorinated hydrocarbons named above, the following chlorinated hydrocarbons are particularly contemplated:

1,1-Dichlorobutan; 1,2-Dichlorbutan; 1,2-Dichlorpropan; 1,3-Dichloropropan; 1,3-Dichloropropylen; 1,2,3-Trichlorpropan; 2-Chlorpentan.

The ratio of chlorosilanes to chlorinated hydrocarbon during the esterification can vary widely. Usually, a chlorosilane to chlorinated hydrocarbon ratio of from 1:1 to 0.5: preferably 1:1 to 1:4, suffices for the achievement of neutral end products and very high yields.

By the invention, the following products, for example, can be obtained: trimethoxysilane, triethoxysilane, tetraethoxysilane, tris-2-methoxyethoxysilane, tetra-2-methoxyethoxysilane, tris-2-methoxyethoxysilane, tetra-2-methoxyethoxysilane, methyldimethoxysilane, methyldiethoxysilane, vinylmethyldiethoxysilane, methyltriethoxysilane, vinyltriethoxysilane, vinyltri-2-methoxyethoxysilane, 3-chloropropyltriethoxysilane, etc.

The esterification is performed in accordance with generally known esterification methods. Preferably the chlorosilane is combined with the chlorinated hydrocarbon and the alcohol is then added portion-wise to the heated mixture. The amount of alcohol to be added is governed by the desired degree of esterification. The reaction is performed preferably at the boiling temperature of the silane-chlorinated hydrocarbon mixture. After separation of the solvent, preferably by distillation, the desired ester is obtained in yields of up to 99%, in a very great purity.

A number of the above-named ester compounds of silicon have achieved an increasing technical importance. For example, a few silicic acid ortho esters are used as binders in zinc dust pigments and in foundry work. Several organic silane esters are used as structural protective agents. A number of other organosilane esters and hydrogen silane esters have a growing technical importance in the synthesis of very valuable organofunctional silanes. In addition, hydrogen silane esters are also of interest in semiconductor chemistry.

In order to more fully illustrate the nature of the invention and the manner of practicing the same, the following examples are presented:

EXAMPLES

EXAMPLE 1

A six-liter three-necked flask was placed in a mushroom heater and equipped with a stirrer, a reflux condenser and a dropping funnel.

1060 g (5 moles) of gamma-chloropropyltrichlorosilane was put into the flask. After the liquid had been heated to 80° C., 930 g (15.5 moles) of n-propanol was added, with vigorous stirring, in portions of 20 ml, the addition being completed in 4½ hours. The mixture was heated for another 4 hours at 90° C., and then the raw product was distilled in vacuo (1–2 Torr at 101° C.). 1015 g (72%) of a colorless product was obtained. When one milliliter of the product was poured into 100 ml of water to which an indicator, methyl orange, had been added, a strong acidity reaction was observed.

EXAMPLE 2

The apparatus was identical to Example 1. 1060 g (5 moles) of gamma-chloropropytrichlorosilane was placed in the flask together with 900 ml of trichloroethylene. The esterification with 15.5 moles of n-propanol was performed the same as in Example 1. After the trichloroethylene had been removed by distillation, a content of 98% of gamma-chloropropyl-tri-(propoxy)-silane was determined in the liquid in the flask, by gas chromatography. When the ester was poured into water containing methyl orange indicator as in Example 1, a neutral reaction was observed.

EXAMPLE 3

The apparatus was identical to Example 1. 1060 g (5 moles) of gamma-chloropropyltrichlorosilane was combined with 900 ml of carbon tetrachloride in the flask. The esterification with 15.5 moles of n-propanol was performed the same as described in Example 1, with refluxing of the carbon tetrachloride. After the carbon tetrachloride had been distilled out, a content of 97.5% of chloropropyltripropoxysilane was determined in the product by gas chromatography. When it was poured into water containing methyl orange indicator, a neutral reaction was indicated.

EXAMPLE 4

1060 g (5 moles) of gamma-chloropropyltrichlorosilane was placed in the flask together with 2.7 l of trichloroethylene. The esterification with 15.5 moles of n-propanol was performed as described in Example 1. After removal of the trichloroethylene by distillation, a content of 98.6% of chloropropyltripropoxysilane was determined by gas chromatography in the product. When the ester was poured into water containing methyl orange indicator, a neutral reaction was indicated.

EXAMPLE 5

The apparatus was identical to Example 1. 785 g (5 moles) of diethyldichlorosilane was placed in the flask. The esterification with 15.5 moles of propano was performed as described in Example 1. The crude ester was purified by distillation in vacuo (20 Torr, 60° C.). 725 grams (71%) of a colorless product was obtained, which upon being poured into water containing methyl orange indicator gave a strong acid reaction as in Example 1.

EXAMPLE 6

The apparatus was identical to Example 1. 785 g (5 moles) of diethyldichlorosilane was placed in the flask together with 2 l of tetrachloroethylene. The esterification with 15.5 moles of n-propanol was performed as described in Example 1. After the tetrachloroethylene was removed by distillation the contents of the flask was analyzed by gas chromatography. A diethyldipropoxysilane content of 97.2% was found. When the product was poured into water containing methyl orange, a neutral raction was indicated.

EXAMPLE 7

The apparatus was identical to Example 1. 745 g (5 moles) of methyltrichlorosilane was placed in the flask and esterified with 1680 g (15.5 moles) of benzyl alcohol as described in Example 1 (initial temperature 60° C., increasing to 80°-85° C. towards the end of the addition of alcohol). The esterification product was refined by vacuum distillation at 1-2 Torr, and 120° C. 1410 g of a colorless fluid (72%) was obtained, which when poured into water containing methyl orange gave a very acid indication.

EXAMPLE 8

The apparatus was identical to Example 1. 745 g (5 moles) of methyltrichlorosilane was placed in the flask together with 1900 ml of tetrachloroethane and esterified with 1680 g (15.5 moles) of benzyl alcohol as described in Example 1. After the chlorinated hydrocarbon was removed by distillation, the contents of the flask was examined by gas chromatography and found to have a content of 98% of methyltribenzyloxysilane. The refinement of the flask contents by vacuum distillation gave 1750 g of a colorless liquid (96.5%) which gave a neutral reaction when poured into water containing methyl orange.

EXAMPLE 9

Apparatus identical to Example 1. 1060 g (5 moles) of gamma-chloropropyltrichlorosilane was combined in the flask with 1900 ml of trichloroethylene and esterified with 906 g (15.5 moles) of isopropanol as described in Example 1. After the trichloroethylene was distilled out, a content of 97.8% of chloropropyltriisopropoxysilane was determined in the liquid in the flask by gas chromatography. A neutral reaction was indicated when the liquid was poured into water containing methyl orange indicator.

EXAMPLE 10

The apparatus was identical to that of Example 1. 815 g (5 moles) of ethyltrichlorosilane was placed in the flask. The esterification was performed with 1180 g (15.5 moles) of methoxyethanol in the manner described in Example 1. The esterification product was then subjected to gas chromatography. A content of 78% of ethyltri-(methoxyethoxy)-silane was determined. In addition, several mixed esters were registered, which were formed by the cleavage of the methoxyethanol to methanol and chloroethanol.

EXAMPLE 11

The apparatus was identical to that of Example 1. 815 g (5 moles) of ethyltrichlorosilane was placed in the flask together with 900 ml of tetrachloroethylene and esterified with 900 ml of tetrachloroethylene and esterified with 1180 g (15.5 moles) of methoxyethanol in the manner described in Example 1. After removal of the tetrachloroethylene by distillation, the contents of the flask was tested by gas chromatography. A content of 97.9% of ethyl-tris-(methoxyethoxy)-silane was determined. No mixed esters were registered. Then the contents of the flask was vacuum distilled (1-2 Torr, 110° C.). 1355 g of ethyl-tris-(methoxyethoxy)-silane was obtained (96%), which when poured into water containing methyl orange indicator gave a neutral reaction.

EXAMPLE 12

The apparatus was identical to that of Example 1. 850 grams (5 moles) of silicon tetrachloride was placed in the flask together with 1900 milliliters of tetrachloroethylene. The esterification is performed as described in Example 1, with 1974 g (21 moles) of phenol.

After removal of the tetrachloroethylene and excess phenol by distillation, the product in the flask was tested by gas chromatography, and was found to contain 98.7% of tetraphenoxysilane.

When the product was poured into water containing methyl orange, a neutral reaction was indicated.

What is claimed is:

1. In a process for the preparation of an alkoxysilane by the esterification of a chlorosilane with an alcohol of the formula R'OH where R' is an alkyl group of 1 to 11 carbon atoms, the improvement which comprises carrying out the process in the presence of a chlorinated hydrocarbon present in the reaction mixture in an amount of 0.5 to 4 times that of solid halogen silane and in the absence of an acid binding agent.

2. A process according to claim 1 wherein the chlorinated hydrocarbon is present in the reaction mixture in an amount from 0.5 to three times that of the halogen silane charged.

3. A process according to claim 1 wherein the alcohol is a primary alcohol, secondary alcohol or phenol.

4. A process according to claim 2 wherein the chlorinated hydrocarbon is present in the reaction mixture in an amount of between 0.1 and 2 that of the halogen silane charged.

5. A process according to claim 1 wherein the hydrogen silane has the formula $R_mSiCl_{4-m}$.

6. A process according to claim 5 wherein the hydrogen silane is selected from the group consisting of trichlorosilane, tetrachlorosilane, methyldichlorosilane, trimethyldichlorosilane, methyltrichlorosilane, ethyltrichlorosilane, ethyldichlorosilane, n-propyldichlorosilane, propyltrichlorosilane, isobutyldichlorosilane, vinyldichlorosilane, vinyltrichlorosilane, vinylmethyldichlorosilane, dimethyldichlorosilane, propenyltrichlorosilane, allyltrichlorosilane, 3-chloropropyltrichlorosilane, phenyltrichlorosilane, chloropropyltrichlorosilane, chloroethyltrichlorosilane, methylchloroethyltrichlorosilane, $CF_3CH_2SiCl_3$ and $CF_3-CH_2-O-(CH_2)_3-SiCl_3$.

7. A process according to claim 1 wherein said chlorinated hydrocarbon is selected from the group consisting of carbon tetrachloride, chloroform, methylene chloride, dichloroethane, dichloroethylene, 1,1,1-trichloroethane, trichloroethylene, perchloroethylene and tetrachloroethane.

8. A process according to claim 7 wherein the chlorinated hydrocarbon is trichloroethane.

9. A process according to claim 7 wherein the chlorinated hydrocarbon is carbon tetrachloride.

10. A process according to claim 7 wherein the chlorinated hydrocarbon is tetrachloroethylene.

11. A process according to claim 7 wherein the chlorinated hydrocarbon is tetrachloroethane.

12. A process according to claim 1 wherein the alcohol is benzyl alcohol.

* * * * *